(12) United States Patent
Hellendahl et al.

(10) Patent No.: US 6,403,593 B1
(45) Date of Patent: Jun. 11, 2002

(54) TRIAZOLE COMPOUNDS AND THE USE THEREOF

(75) Inventors: Beate Hellendahl, Schifferstadt; Annegret Lansky, Darmstadt, both of (DE); Rainer Munschauer, Shrewsbury, MA (US); Siegfried Bialojan, Ofstersheim (DE); Liliane Unger, Ludwigshafen (DE); Hans-Jürgen Teschendorf, Dundenhofen (DE); Karsten Wicke, Altrip (DE); Karla Drescher, Dossenheim (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/481,976

(22) Filed: Jan. 13, 2000

Related U.S. Application Data

(62) Division of application No. 08/765,916, filed as application No. PCT/EP95/02781 on Feb. 14, 1995.

(51) Int. Cl.[7] .................. C07D 403/12; C07D 403/06; A61K 31/495
(52) U.S. Cl. .................. 514/254.05; 544/366; 544/121; 544/295; 544/212; 514/236.2; 514/252.11; 514/252.19; 514/245
(58) Field of Search ................. 544/366, 121, 544/295, 212; 514/254.05, 236.2, 252.11, 252.19, 245

(56) References Cited

U.S. PATENT DOCUMENTS

| | | | |
|---|---|---|---|
| 4,338,453 A | 7/1982 | Gall et al. | 548/263 |
| 4,408,049 A | 10/1983 | Gall et al. | 544/360 |
| 4,487,773 A | 12/1984 | Temple, Jr. et al. | 424/250 |
| 4,575,555 A | 3/1986 | Temple et al. | 546/276 |
| 4,577,020 A | 3/1986 | Gall et al. | 544/366 |
| 4,613,600 A | 9/1986 | Gammans et al. | 514/252 |
| 4,711,885 A | 12/1987 | Wierzbicki et al. | 514/253 |
| 4,886,805 A | 12/1989 | Bru-Magniez et al. | 514/253 |

FOREIGN PATENT DOCUMENTS

| | | |
|---|---|---|
| EP | 0199641 | 10/1986 |
| EP | 0254623 | 1/1988 |
| EP | 0568437 | 11/1993 |
| GB | 1053085 | 12/1966 |

OTHER PUBLICATIONS

Czarnocka–Janowicz et al, Chemical Abstrasts vol. 115 Entry 49519 (1991).*
Sokoloff et al., Nature 347, pp. 146–151 (Sep. 1990).
Reitz et al., J. Med. Chem. 37, pp. 1060–1062 (1994).
Milan et al., J. Pharm. Exp. Therapeutics 275, 885–898 (1995).

* cited by examiner

*Primary Examiner*—John M. Ford
(74) *Attorney, Agent, or Firm*—Keil & Weinkauf

(57) ABSTRACT

The present invention relates to triazole compounds of the following formula:

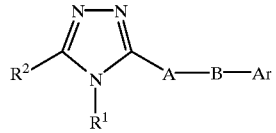

where $R^1$, $R^2$, A, B and Ar have the meanings stated in the description. The compounds according to the invention have a high affinity for the dopamine $D_3$ receptor and can therefore be used to treat disorders which respond to dopamine $D_3$ ligands.

19 Claims, No Drawings

TRIAZOLE COMPOUNDS AND THE USE THEREOF

This application is a divisional application of U.S. application Ser. No. 08/765,916 (allowed), filed Jan. 14, 1997, under 35 U.S.C. §371 as a national stage application of Internation Application No. PCT/EP 95/02,781, which was filed Jul. 14, 1995.

The invention relates to triazole compounds and to the use of such compounds. Said compounds have valuable therapeutic properties and can be used to treat disorders which respond to dopamine $D_3$ receptor ligands, Compounds which are of the type under discussion here and have physiological activity have been disclosed. U.S. Pat. Nos. 4,338,453, 4,408,049 and 4,577,020 describe triazole compounds which have antiallergic activity.

Neurons receive their information inter alia via G protein-coupled receptors. There are numerous substances which exert their effect via these receptors. One of them is dopamine.

Confirmed findings on the presence of dopamine and its physiological function as neurotransmitter have been published. Cells which respond to dopamine are connected with the etiology of schizophrenia and Parkinson's disease. These and other disorders are treated with drugs which interact with dopamine receptors.

By 1990, two subtypes of dopamine receptors had been clearly defined pharmacologically, namely $D_1$ and $D_2$ receptors.

Sokoloff et al., Nature 1990, 347: 146–151, found a third subtype, namely $D_3$ receptors. They are expressed mainly in the limbic system. The $D_3$ receptors differ structurally from the $D_1$ and $D_2$ receptors in about half the amino-acid residues.

The effect of neuroleptics has generally been ascribed to their affinity for $D_2$ receptors. Recent receptor-binding studies have confirmed this. According to these, most dopamine antagonists, like neuroleptics, have high affinity for $D_2$ receptors but only low affinity for $D_3$ receptors.

We have now found, surprisingly, that the compounds according to the invention have a high affinity for the dopamine $D_3$ receptor and only a low affinity for the $D_2$ receptor. They are thus selective $D_3$ ligands.

The present invention therefore relates to triazole compounds of the formula I:

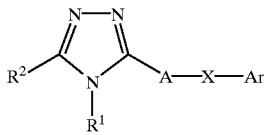

where

A is a straight-chain or branched $C_1$–$C_{18}$-alkylene group which may comprise at least one group selected from O, S, $NR^3$, $CONR^3$, $NR^3CO$, COO, OCO, $C_3$–$C_6$-cycloalkylene or a double or triple bond, X is a radical of the formula:

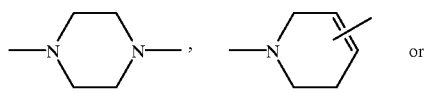

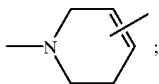

$R^1$ is H, $CO_2R^3$, $NR^3R^4$, $OR^4$, $C_3$–$C_6$-cycloalkyl or $C_1$–$C_8$-alkyl which is unsubstituted or substituted by OH, $OC_1$–$C_8$-alkyl or halogen;

$R^2$ has the meanings indicated for $R^1$ or is $CF_3$, $SR^3$, halogen or CN;

$R^3$ is H or $C_1$–$C_8$-alkyl which is unsubstituted or substituted by OH, $OC_1$–$C_8$-alkyl, phenyl or halogen;

$R^4$ has the meanings indicated for $R^3$ or is $COR^3$ or $CO_2R^3$;

Ar is phenyl, pyridyl, pyrimidyl or triazine, where AR may have from one to four substituents which are selected, independently of one another, from $OR^4$, $C_1$–$C_8$-alkyl, $C_2$–$C_6$-alkenyl, $C_2$–$C_6$-alkynyl, halogen, CN, $CO_2R^3$, $NO_2$, $SO_2R^3$, $SO_3R^3$, $NR^3R^4$, $SO_2NR^3R^4$, $SR^3$, $CF_3$, $CHF_2$, a 5- or 6-membered carbocyclic aromatic or nonaromatic ring and a 5- or 6-membered heterocyclic aromatic or nonaromatic ring having 1 to 4 hetero atoms selected from O, S and N, where the carbocyclic or heterocyclic ring may be unsubstituted or substituted by $C_1$–$C_8$-alkyl, halogen, $OC_1$–$C_8$-alkyl, OH, $NO_2$ or $CF_3$ and where Ar may also be fused to a carbocyclic or heterocyclic ring of the type defined above, and the salts thereof with physiologically tolerated acids.

The compounds according to the invention are selective dopamine $D_3$ receptor ligands which intervene regioselectively in the limbic system and, because of their low affinity for the $D_2$ receptor, have fewer side effects than classical neuroleptics, which are $D_2$ receptor antagonists. The compounds can therefore be used to treat disorders which respond to dopamine $D_3$ receptor antagonists or agonists, eg. for treating disorders of the central nervous system, in particular schizophrenia, depression, neuroses and psychoses. They can additionally be used to treat sleep disorders and nausea and as antihistamines.

Within the scope of the present invention, the following terms have the meanings indicated below:

Alkyl (also in radicals such as alkoxy, alkyl-amino etc.) means a straight-chain or branched alkyl group having 1 to 8 carbon atoms, preferably 1 to 6 carbon atoms and, in particular, 1 to 4 carbon atoms. The alkyl group can have one or more substituents which are selected, independently of one another, from OH and $OC_1$–$C_8$-alkyl.

Examples of an alkyl group are methyl, ethyl, n-propyl, i-propyl, n-butyl, isobutyl, t-butyl etc.

Alkylene stands for straight-chain or branched radicals having, preferably, 2 to 15 carbon atoms, particularly preferably 3 to 10 carbon atoms.

The alkylene groups may comprise at least one of the abovementioned groups. This can—just like the double or triple bond mentioned—be arranged in the alkylene chain at any point or at the end of the chain so that it connects the chain to the triazole residue. The latter is preferred. When the alkylene group comprises a double or triple bond, it has at least three carbon atoms in the chain.

Halogen is F, Cl, Br, I and, in particular, Cl, Br, I.

$R^1$ and $R^2$ are preferably, independently of one another, H, $C_1$–$C_8$-alkyl, $NR^3R^4$ or $OR^4$.

Ar can have one, two, three or four substituents. They are preferably selected, independently of one another, from halogen, $CF_3$, $CHF_2$, $NR^3R^4$, $OR^4$, $NO_2$, $C_1$–$C_8$-alkyl, $OC_1$–$C_8$-alkyl, $SR^3$ and CN, where $R^3$ and $R^4$ have the abovementioned meanings.

If one of the substituents of Ar is $C_1$–$C_8$-alkyl, a branched radical, in particular the isopropyl or t-butyl group, is preferred.

Ar preferably has at least one substituent and is, in particular,

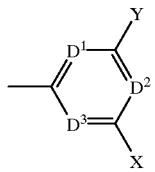

where $D^1$, $D^2$ and $D^3$ are, independently of one another, CR or N, and R, X and Y are H or are the substituents of the radical Ar indicated above or below.

Ar is preferably unsubstituted or substituted phenyl, 2-, 3- or 4-pyridinyl or 2-, 4(6)- or 5-pyrimidyl.

When one of the substituents of the radical Ar is a 5- or 6-membered heterocyclic ring, examples thereof are a pyrrolidine, piperidine, morpholine, piperazine, pyridine, pyrimidine, triazine, pyrrole, thiophene, thiazole, imidazole, oxazole, isoxazole, pyrazole or thiadiazole residue.

When one of the substituents of the radical Ar is a carbocyclic radical, it is, in particular, a phenyl, cyclopentyl or cyclohexyl radical.

When Ar is fused to a carbocyclic or heterocyclic radical, Ar is, in particular, a naphthalene, di- or tetrahydronaphthalene, quinoline, di- or tetrahydroquinoline, indole, dihydroindole, benzimidazole, benzothiazole, benzothiadiazole, benzopyrrole or benzotriazole residue.

X is preferably

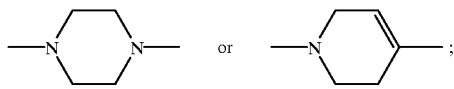

A preferred embodiment comprises compounds of the formula I where A is $C_3$–$C_{10}$-alkylene which comprises at least one group which is selected from O, S, $NR^3$, cyclohexylene, in particular 1,4-cyxclohexylene, and a double or triple bond, where $R^3$ is as defined above.

Another preferred embodiment comprises compounds of the formula I where
- $R^1$ is H, $OR^4$ where $R^4$ is H or $C_1$–$C_8$-alkyl, or $C_3$–$C_6$-cycloalkyl or $C_1$–$C_8$-alkyl which is unsubstituted or substituted by OH, $OC_1$–$C_8$-alkyl or halogen;
- $R^2$ is H, $C_1$–$C_8$-alkyl which is unsubstituted or substituted by OH, $OC_1$–$C_8$-alkyl or halogen, or $NR^3R^4$ where $R^3$ and $R^4$ are, independently of one another, H, phenyl-$C_1$–$C_8$-alkyl or $C_1$–$C_8$-alkyl, or $OR^4$ where $R^4$ is H or $C_1$–$C_8$-alkyl, or $CF_3$;
- A is as defined in claim 3, and
- Ar is phenyl, pyridyl or pyrimidyl which may have one, two, three or four substituents which are selected from H, $C_1$–$C_8$-alkyl which is unsubstituted or substituted by OH, $OC_1$–$C_8$-alkyl or halogen, or $OR^4$ where $R^4$ is H, $C_1$–$C_6$-alykl [sic] which is unsubstituted or substituted by OH, $OC_1$–$C_8$-alkyl or halogen, or $CHF_2$, $CF_3$, CN, Halogen, $C_2$–$C_6$-alkenyl, $C_2$–$C_6$-alkynyl, phenyl, naphthyl and a 5- or 6-membered heterocyclic aromatic radical with 1 to 3 hetero atoms selected from O, N and S.

Another preferred embodiment comprises compounds of the formula I where
- $R^1$ is H or $C_1$–$C_8$-alkyl which is unsubstituted or substituted by OH, $OC_1$–$C_8$-alkyl or halogen;
- $R^2$ is H, $C_1$–$C_8$-alkyl which is unsubstituted or substituted by OH, $OC_1$–$C_8$-alkyl or halogen, or $NR^3R^4$ where $R^3$ and $R^4$ are, independently of one another, H or $C_1$–$C_8$-alkyl, or $OR^4$ where $R^4$ is H or $C_1$–$C_8$-alkyl, or $CF_3$;
- A is $C_1$–$C_{10}$-alkylene which may comprise and oxygen or sulfur atom or the group $NR^3$ where $R^3$ is as defined above;
- Ar is phenyl which may have one to four substituents which are selected, independently of one another, from H, CN, $SR^3$, halogen, $C_1$–$C_8$-alkyl which is unsubstituted or substituted by OH, $OC_1$–$C_8$-alkyl or halogen, or phenyl, naphthyl, $OR^4$, $NO_2$, $NR^3R^4$, $CHF_2$ and $CF_3$, where $R^3$ and $R^4$ have the stated meanings.

Particularly preferred in this connection are the compounds of the formula I where
- A is $SC_3$–$C_{10}$-alkylene, $OC_3$–$C_{10}$-alkylene or $NR^3$—$C_3$–$C_{10}$-alkylene, where $R^3$ is H or $C_1$–$C_8$-alkyl,
- $R^1$ is H or $C_1$–$C_8$-alkyl;
- $R^2$ has the abovementioned meanings;
- X is

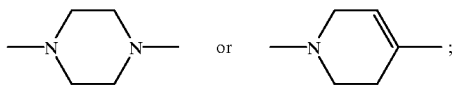

Ar is phenyl which has one to four substituents which are, independently of one another, H, $C_1$–$C_8$-alkyl, $OC_1$–$C_8$-alkyl, $CHF_2$, $CF_3$ or CN.

Ar has, in particular, two substituents which are located in positions 3 and 5, with one substituents being $CF_3$, $CHF_2$ or $C_1$–$C_8$-alkyl and the other substituent being H or $C_1$–$C_8$-alkyl.

Another preferred embodiment comprises compounds of the formula I where
- Ar is pyrimidinyl which has one to three substituents which are selected, independently of one another, from H, $C_1$–$C_8$-alkyl, phenyl, naphthyl, $C_3$–$C_6$-cycloalky, OH, $OC_1$–$C_8$-alkyl, halogen, CN, $CF_3$, $CHF_2$ and a 5- or 6-membered heterocyclic aromatic radical with 1 to 3 hetero atoms selected from O, N and S;
- $R^1$ is H or $C_1$–$C_8$-alkyl which is unsubstituted or substituted by OH, $OC_1$–$C_8$-alkyl or halogen,
- $R^2$ is H, $NR^3R^4$ or $OR^4$ where $R^3$ and $R^4$ are, independently of one another, H, $C_1$–$C_8$-alkyl or phenyl-$C_1$–$C_8$-alkyl;
- A is $C_1$–$C_{10}$-alkylene which may comprise at least one group selected from O, S, $NR_3$ where $R^3$ is H or $C_1$–$C_8$-alkyl, and a double or triple bond; and
- X is as defined above.

Another preferred embodiment comprises compounds of the formula I where
- Ar is pyridinyl which has one to four substituents which are selected, independently of one another, from H, $C_1$–$C_8$-alkyl, phenyl, naphthyl, OH, $OC_1$–$C_8$-alkyl, halogen, $CF_3$, CN, $C_2$–$C_6$-alkenyl, $C_2$–$C_6$-alkynyl and a 5- or 6-membered heterocyclic aromatic radical with 1 to 3 hetero atoms selected from O, N and S;
- $R^1$ is H, $C_1$–$C_8$-alkyl, $C_3$–$C_6$-cycloalkyl or $OR^4$ where $R^4$ is H or $C_1$–$C_8$-alkyl which is unsubstituted or substituted by OH, $OC_1$–$C_8$-alkyl or halogen; and $R^2$, A and X are as defined above.

The invention also embraces the acid addition salts of the compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Other acids which can be used are described in Fortschritte der Arzneimittelforschung, Volume 10, pages 224 et seq., Birkhäuser Verlag, Basle and Stuttgart, 1996.

The compounds of the formula [sic] I may have one or more centers or asymmetry. The invention therefore includes not only the racemates but also the relevant enantiomers and diastereomers. The invention also includes the tautomeric forms in each case.

The compounds of the formula [sic] I can be prepared by methods similar to conventional ones as described, for example, in Houben Weyl "Handbuch der Organischen Chemie", 4th Ed., Thieme Verlag, Stuttgart 1994, Volume E8/d, pages 479 et seq.; and A. R. Katritzky, C. W. Rees (ed.) "Comprehensive Heterocyclic Chemistry", 1st Ed. Pergamon Press 1984, in particular Vol. 5, part 4a, pages 733 et seq. and literature cited therein. The process for preparing the compounds comprises i) reacting a compound of the general formula II:

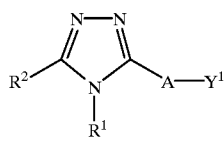

where Y is a conventional leaving group, with a compound of the general formula III

ii) to prepare a compound of the formula I where A is an oxygen or sulfur atom or $NR^3$:

a) reacting a compound of the general formula IV:

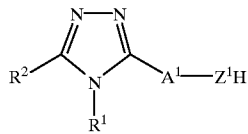

where $Z^1$ is O, S or $NR^3$ and $A^1$ is $C_0$–$C_{18}$-alkylene, with a compound of the general formula VI

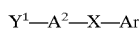

where $Y^1$ has the abovementiones meanings, and $A^2$ is $C_1$–$C_{18}$-alkylene, where $A^1$ and $A^2$ together have 1 to 18 carbon atoms;

iii) to prepare a compound of the formula I where A comprises the group COO or $CONR^3$:

a) reacting a compound of the general formula VII:

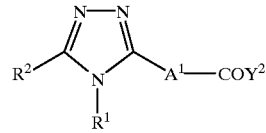

where $Y^2$ is OH, $OC_1$–$C_8$-alkyl, Cl or, together with CO, is an activated carboxyl group, and $A^1$ has the abovementioned meanings, with a compound of the formula VIII:

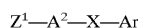

where $A^2$ has the abovementioned meanings, and $Z^1$ is OH or $NHR^3$, iv) to prepare a compound of the formula I where A comprises the group OCO or $NR^3CO$:

a) reacting a compound of the formula IV

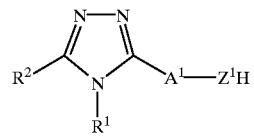

where $Z^1$ is O or $NR^3$, with a compound of the formula X:

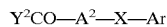

where X and $Y^2$ have the abovementioned meanings, and where $R^1$, $R^2$, A, X and Ar have the abovementioned meanings.

The reactions described above generally take place in a solvent at from room temperature to the boiling point of the solvent used. Examples of solvents which can be used are ethyl acetate, tetrahydrofuran, dimethylformamide, dimethoxyethane, toluene, xylene or a ketone, such as acetone or methyl ethyl ketone.

An acid acceptor is present if required. Suitable acid acceptors are inorganic bases such as sodium or potassium carbonate, sodium methoxide, sodium ethoxide, sodium hydride or organic bases such as triethylamine or pyridine. The latter may also serve as solvents.

The crude product is isolated in a conventional way, for example by filtration, removal of the solvent by distillation or extraction from the reaction mixture. The resulting compound can be purified in a conventional way, for example by recrystallization from a solvent, chromatography or conversion into an acid addition compound.

The acid addition salts are prepared in a conventional way by mixing the free base with the appropriate acid, possibly in solution in an organic solvent, for example a lower alcohol such as methanol, ethanol or propanol, an ether such as methyl t-butyl ether, a ketone such as acetone or methyl ethyl ketone, or an ester such as ethyl acetate.

The abovementioned starting materials are disclosed in the literature or can be prepared by known processes.

To treat the abovementioned disorders, the compounds according to the invention are administered in a conventional manner orally or parenterally (subcutaneously, intravenously, intramuscularly, intraperitoneally). Administration can also take place with vapors or sprays through the nasopharyngeal space.

The dosage depends on the age, condition and weight of the patient and on the mode of administration. As a rule, the daily dose of active substance is about 10 to 1000 mg per patient and day on oral administration and about 1 to 500 mg per patient and day on parenteral administration.

The invention also relates to pharmaceutical compositions which contain the compounds according to the invention. These compositions are in the usual solid or liquid pharmaceutical administration forms, for example as tablets, film-coated tablets, capsules, powders, granules, sugar-coated tablets, suppositories, solutions or sprays. The active substances can in these cases be processed with conventional pharmaceutical aids such as tablet binders, fillers, preservatives, tablet disintegrants, flow regulators, plasticizers, wetting agents, dispersants, emulsifiers, solvents, release-slowing agents, antioxidants and/or propellant gases (cf. H. Sucker et al., Pharmaceutics Technologie, Thieme-Verlag, Stuttgart, 1978). The administration forms obtained in this way normally contain the active substance in an amount from 1 to 99% by weight.

The following examples serve to explain the invention without limiting it.

EXAMPLE 1

4-Methyl-3-[3-(4-{3-trifluoromethylphenyl}piperazinyl)propylmercapto]-4H-1,2,4-triazole

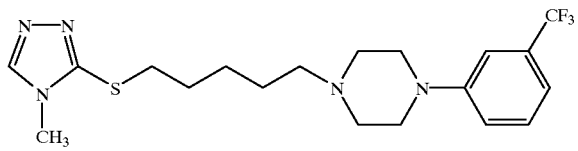

a) 1-(3-Chloropropyl)-4-(3-trifluoromethylphenyl)piperazine 30 g (0.13 mol) of m-trifluoromethylphenylpiperazine, 23 g (0.146 mol) of 1,3-bromochloropropane [sic ] and 15 g (0.148 mol) of triethylamine in 200 ml of THF were refluxed for 4 hours. Cooling was followed by filtration with suction and concentration. The viscous residue was taken up in ethyl acetate, washed with water, dried over $MgSO_4$ and then concentrated. The resulting residue comprised 39 g of product as yellowish oil (quantitative yield).

b) 4-Methyl-3-[3-(4-{3-trifluoromethylphenyl}piperazinyl)propylmercapto]-4H-1,2,4-triazole 1.15 g (10 mmol) of 3-mercapto-4-methyl-4H-1,2,4-triazole, 3.1 g (10.1 mmol) of 1-(3-chloropropyl)-4-(3-trifluoromethylphenyl)piperazine and 1.5 g (15 mmol) of triethylamine in 5 ml of DMF were stirred at 100° C. for 1 hour. The mixture was then poured into 5% strength hydrochloric acid and extracted with ethyl acetate. The aqueous phase was made alkaline with sodium hydroxide solution and then extracted again with ethyl acetate, and the organic phase was dried over $MgSO_4$ and concentrated. The residue was purified by chromatography (mobile phase: $CH_2Cl_2$/$CH_3OH$=95/5). 2.1 g of product were obtained as a yellowish oil (=55% yield).

H-NMR [δ, ppm]: 2.02 (2H); 2.55 (2H); 2.61 (4H); 3.23 (6H); 3.33 (2H); 3.61 (3H); 7.06 (3H); 7.33 (1H); 8.12 (1H)

EXAMPLE 2

4-Methyl-3-[5-(4-{3-trifluoromethylphenyl}piperazinyl)pentylmercapto]-4H-1,2,4-triazole

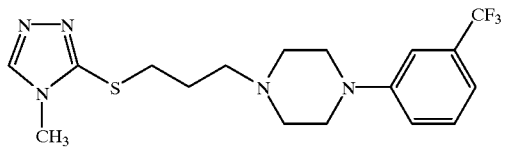

a) 3-(5-Chloropentylmercapto)-4-methyl-4H-1,2,4-triazole 2.88 g (25 mmol) of 3-mercapto-4-methyl-4H-1,2,4-triazole, 4.64 g (25 mmol) of 1,5-bromochloropentane [sic] and 5.58 g (25.5 mmol) of triethylamine in 100 ml of THF were refluxed for 4 hours. Cooling was followed by filtration with suction, concentration and purification of the residue by chromatography (mobile phase: $CH_2Cl_2$/$CH_3OH$=95/5). 1.9 g of product were obtained (=35% yield).

b) 4-Methyl-3-[5-(4-{3-trifluoromethylphenyl}piperazinyl)pentylmercapto]-4H-1,2,4-triazole 1.9 g (8.66 mmol) of product from 2a), 2.19 g (9.52 mmol) of m-trifluoromethylphenylpiperazine and 0.96 g (9.52 mmol) of triethylamine in 5 ml of DMF were stirred at 90° C. for 5 hours. The mixture was then poured into water and extracted three times with $CH_2Cl_2$, and the organic phase was dried over $MgSO_4$ and concentrated. The residue was mixed with methyl t-butyl ether and filtered with suction, and the mother liquor was concentrated. Purification by chromatography (mobile phase: $CH_2Cl_2$/$CH_3OH$=95/5) resulted in 2.1 g of product (=59% yield). Melting point 70–76° C.

The following compounds were prepared in a similar way:

| No. | Example | Physical data, H-NMR [δ, ppm] melting point [° C.] |
|---|---|---|
| 3 | triazole(NH, NH₂)-S-CH₂CH₂CH₂-piperazine-phenyl-CF₃ | 1.83(2H); 2.45(6H); 3.0(2H); 3.27(4H); 6.0(2H); 7.05(1H); 7.15(1H); 7.2(1H); 7.4(1H); 11.95(1H) |
| 4 | triazole(CH₃, NH₂)-S-CH₂CH₂CH₂-piperazine-phenyl-CF₃ | 1.85(2H); 2.3(3H); 2.45(2H); 2.5(4H); 3.1(2H); 3.2(4H); 5.8(2H); 7.05(1H); 7.15(1H); 7.2(1H); 7.41(1H) |
| 5 | triazole(NH)-S-CH₂CH₂CH₂-piperazine-phenyl-CF₃ | 2.1(2H); 2.7(6H); 3.22(2H); 3.42(4H); 7.1(3H); 7.38(1H); 7.92(1H) |
| 6 | triazole(CF₃, NH)-S-CH₂CH₂CH₂-piperazine-phenyl-CF₃ | 200–205 |
| 7 | triazole(CF₃, CH₃)-S-CH₂CH₂CH₂-piperazine-phenyl-CF₃ | 2.05(2H); 2.55(2H); 2.6(4H); 3.23(4H); 3.4(2H); 3.65(3H); 7.08(3H); 7.35(1H) |
| 8 | triazolone(CH₃)-S-CH₂CH₂CH₂-piperazine-phenyl-CF₃ | 2.0(2H); 2.53(2H); 2.6(4H); 3.13(2H); 3.25(7H); 7.08(3H); 7.35(1H); 9.88(1H) |
| 9 | triazolone(iPr)-S-CH₂CH₂CH₂-piperazine-phenyl-CF₃ | 1.5(6H); 1.98(2H); 2.55(2H); 2.62(4H); 3.15(2H); 3.22(4H); 4.32(1H); 7.08(3H); 7.35(1H); 10.0(1H) |
| 10 | triazole(NH₂, CH₃)-S-CH₂CH₂CH₂-piperazine-phenyl-CF₃ | 1.95(2H); 2.5(2H); 2.58(4H); 3.1(2H); 3.22(4H); 3.4(3H); 4.4(2H); 7.08(3H); 7.35(1H) |
| 11 | triazole(NH₂, CH₃)-S-CH₂-CH=CH-piperazine-phenyl-CF₃ | 2.52(4H); 3.0(2H); 3.22(4H); 3.4(3H); 3.64(2H); 4.96(2H); 5.62(1H); 5.72(1H); 7.05(3H); 7.3(1H) |

-continued

| No. | Example | Physical data, H-NMR [δ, ppm] melting point [° C.] |
|---|---|---|
| 12 | ![structure 12: 5-amino-4-methyl-1,2,4-triazole-3-thio-(CH₂)₃-piperazine-(3-CHF₂-phenyl)] | 1.95(2H); 2.52(2H); 2.6(4H); 3.12(2H); 3.22(4H); 3.4(3H); 4.2(2H); 6.6(1H); 7.0(3H); 7.35(1H) |
| 13 | ![structure 13: 5-amino-4-methyl-1,2,4-triazole-3-thio-(CH₂)₃-piperazine-(3,5-diethylphenyl)] | 1.15(6H); 1.75(2H); 2.45(10H); 2.9(2H); 3.08(4H); 3.3(3H); 5.95(2H); 6.45(1H); 6.55(2H) |
| 14 | ![structure 14: 5-amino-4-methyl-1,2,4-triazole-3-thio-(CH₂)₃-piperazine-(2-naphthyl)] | 166–171 |
| 15 | ![structure 15: 5-amino-4-methyl-1,2,4-triazole-3-thio-(CH₂)₃-piperazine-(3,5-di-tert-butylphenyl)] | 1.25(18H); 1.75(2H); 2.4(2H); 2.45(4H); 2.9(2H); 3.1(4H); 3.35(3H); 5.95(2H); 6.75(2H); 6.88(1H) |

The compounds according to the invention which are compiled in Tables 1 to 3 below were obtained in a similar manner.

The compounds compiled in Tables 4 to 8 below can likewise be obtained in a similar manner.

TABLE 1

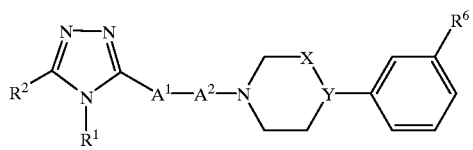

| Example No. | $R^1$ | $R^2$ | $R^6$ | X—Y | $A^1$ | $A^2$ |
|---|---|---|---|---|---|---|
| 16 | $CH_3$ | $NH_2$ | i Prop | $CH_2$—N | S | —$(CH_2)_3$— |
| 17 | $CH_3$ | $NH_2$ | $CF_3$ | $CH_2$—N | S | —$(CH_2)_2CH$=$CH(CH_2)_2$— |
| 18 | $CH_3$ | $NH_2$ | $CF_3$ | $CH_2$—N | S | —$(CH_2)_2$— |
| 19 | $CH_3$ | $NH_2$ | $CF_3$ | $CH_2$—N | S | —$CH_2C(CH_3)$=$CHCH_2$— |
| 20 | $CH_3CH_2$ | $NH_2$ | $CF_3$ | $CH_2$—N | S | —$(CH_2)_3$— |
| 21 | $CH_3$ | $NH_2$ | $CF_3$ | $CH_2$—N | S | 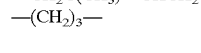 —$CH_2$—(cyclohexyl)—$CH_2$— |
| 22 | n Prop | $NH_2$ | $CF_3$ | $CH_2$—N | S | —$(CH_2)_3$— |
| 23 | i Prop | $NH_2$ | $CF_3$ | $CH_2$—N | S | —$(CH_2)_3$— |

TABLE 1-continued

Structure: R²-[1,2,4-triazole with N-R¹]-A¹-A²-N[piperazine with X,Y]-phenyl-R⁶

| Example No. | R¹ | R² | R⁶ | X—Y | A¹ | A² |
|---|---|---|---|---|---|---|
| 24 | CH₃CH₂ | NH₂ | CHF₂ | CH₂—N | S | —(CH₂)₃— |
| 25 | n Prop | NH₂ | CHF₂ | CH₂—N | S | —(CH₂)₃— |
| 26 | CH₃CH₂ | NH₂ | i Prop | CH₂—N | S | —(CH₂)₃— |
| 27 | n Prop | NH₂ | i Prop | CH₂—N | S | —(CH₂)₃— |
| 28 | i Prop | NH₂ | i Prop | CH₂—N | S | —(CH₂)₃— |
| 29 | CH₃ | NH₂ | CF₃ | CH₂—N | S | —(CH₂)₇— |
| 30 | CH₃ | NH₂ | CF₃ | CH₂—N | S | —(CH₂)₈— |
| 31 | CH₃ | NH₂ | i Prop | CH₂—N | S | —(CH₂)₉— |
| 32 | CH₃ | NH₂ | CF₃ | CH₂—N | S | —(CH₂)₄O(CH₂)₄— |
| 33 | CH₃ | NH₂ | i Prop | CH₂—N | S | —(CH₂)₄O(CH₂)₄— |
| 34 | CH₃ | NHCH₃ | CF₃ | CH₂—N | S | —(CH₂)₃— |
| 35 | CH₃ | NH₂ | i Prop | CH₂—N | S | —CH₂C(CH₃)=CHCH₂— |
| 36 | CH₃ | NH₂ | CF₃ | CH=N | S | —(CH₂)₃— |
| 37 | CH₃ | NHCH₃ | CHF₂ | CH₂—N | S | —(CH₂)₃— |

TABLE 2

Structure: R²-[1,2,4-triazole with N-R¹]-A¹-A²-N[piperazine with X,Y]-pyrimidine with R⁶, D, R⁸

| Example No. | R¹ | R² | R⁶ | D | R⁸ | X—Y | A | B |
|---|---|---|---|---|---|---|---|---|
| 38 | CH₃ | NH₂ | CF₃ | CH | H | CH₂—N | S | —(CH₂)₃— |
| 39 | CH₃ | NH₂ | Cl | CH | CF₃ | CH₂—N | S | —(CH₂)₃— |
| 40 | CH₃ | NH₂ | t But | N | CF₃ | CH₂—N | S | —(CH₂)₃— |
| 41 | CH₃ | NH₂ | 1-Pyrrolyl | N | CH₃ | CH₂—N | S | —(CH₂)₃— |
| 42 | CH₃ | NH₂ | t But | N | CF₃ | CH₂—N | S | —CH₂C(CH₃)=CHCH₂— |
| 43 | CH₃ | NH₂ | t But | N | CF₃ | CH₂—N | S | —(CH₂)₃— |
| 44 | CH₃ | NH₂ | t but | N | t But | CH₂—N | S | —(CH₂)₃— |
| 45 | CH₃ | NH₂ | i Prop | C—CN | i Prop | CH₂—N | S | —(CH₂)₃— |

TABLE 3

Physical data of the compounds of Examples 16–45

| Example No. | Mp. °C. | ¹H—NMR |
|---|---|---|
| 16 | | 1.2 (6H); 1.9 (2H); 2.5 (6H); 2.8 (1H); 3.2 (6H); 3.5 (3H); 4.4 (2H); 6.7 (3H); 7.1 (1H) |
| 17 | 194–196° Dihydrochloride | |
| 18 | 109–110° Hydrochloride | |
| 19 | 132–134° | |
| 20 | | 1.3 (3H); 2.0 (2H); 2.5 (6H); 3.2 (6H); 3.8 (2H; 4.6 (2H); 7.0 (3H); 7.4 (1H) |
| 21 | 154–155° | |
| 22 | | 1.0 (3H); 1.8 (2H); 2.0 (2H); 2.5 (6H); 3.1 (6H); 3.7 (2H); 4.4 (2H); 7.0 (3H); 7.3 (1H) |
| 23 | | 1.2 (6H); 2.0 (2H); 2.3 (6H); 3.1 (6H); 4.1 (2H); 4.3 (1H); 7.0 (3H); 7.2 (1H) |
| 24 | | 1.2 (3H); 1.8 (2H); 2.4 (2H) 2.5 (4H); 2.9 (2H); 3.1 (4H); 3.8 (2H); 6.0 (2H); 6.9 (1H); 7.0 (3H); 7.3 (1H) |
| 25 | | 1.0 (3H); 1.7 (2H); 2.0 (2H); 2.5 (2H); 2.6 (4H); 3.0 (6H), 3.7 (2H), 4.6 (2H); 6.6 (1H); 7.0 (3H); 7.4 (1H) |
| 26 | | 1.2 (9H); 1.9 (2H); 2.5 (2H); 2.6 (4H); 2.9 (1H); 3.15 (6H); 3.8 (2H); 6.8 (3H); 7.2 (1H) |
| 27 | | 0.9 (3H); 1.2 (6H), 1.7 (2H); 1.9 (2H); 2.5 (2H); |

TABLE 3-continued

Physical data of the compounds of Examples 16–45

| Example No. | Mp. ° C. | $^1$H—NMR |
|---|---|---|
|  |  | 2.6 (4H); 2.8 (1H); 2.9 (2H); 3.2 (4H); 3.4 (2H); 6.8 (3H); 7.3 (1H) |
| 28 |  | 1.2 (6H); 1.5 (6H); 1.9 (2H); 2.4 (2H); 2.5 (4H); 2.8 (1H); 3.2 (6H), 4.3 (3H); 6.75 (3H), 7.15 (1H) |
| 29 | 118–119° |  |
| 30 | 164–166° Fumarate |  |
| 31 |  | 1.2 (6H); 1.4 (14H), 1.7 (2H); 2.4 (2H), 2.6 (4H), 2.8 (1H); 3.0 (2H); 3.2 (4H), 3.4 (3H), 4.6 (2H), 6.8 (3H); 7.2 (1H) |
| 32 |  | 1.7 (8H); 2.4 (2H); 2.6 (4H); 3.0 (2H; 3.3 (4H); 3.5 (7H); 4.8 (2H); 7.1 (3H); 7.3 (1H) |
| 33 |  | 1.2 (6H); 1.6 (8H); 2.4. (2H); K 2.6 (4H); 2.9 (1H); 3.1 (2H); 3.2 (4H); 3.3 (7H); 4.8 (2H); 6.8 (3H); 7.2 (1H) |
| 34 | 234–270° Trihydrochloride |  |
| 35 | 126–129° |  |
| 36 | 93–100° |  |
| 37 | 234–235° Dihydrochloride |  |
| 38 | 153–155° |  |
| 39 | 116–118° |  |
| 40 | 51–60° |  |
| 41 | 65–67° |  |
| 42 | 67–72° |  |
| 43 | 121–126° |  |
| 44 | 180–183° Fumarate |  |
| 45 | 130–133° |  |

TABLE 4

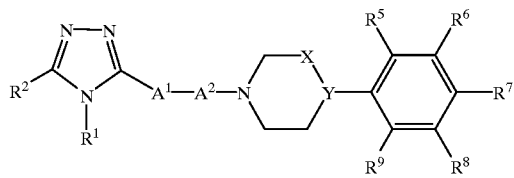

| Example No. | R1 | R2 | R5 | R6 | R7 | R8 | R9 | X—Y | A$^1$ | A$^2$ |
|---|---|---|---|---|---|---|---|---|---|---|
| 46 | CH$_3$ | NH$_2$ | H | tBut | H | Me | H | CH$_2$—N | S | —(CH$_2$)$_3$— |
| 47 | CH$_3$ | NH$_2$ | H | tBut | H | Ph | H | CH$_2$—N | S | —(CH$_2$)$_3$— |
| 48 | CH$_3$ | NH$_2$ | H | tBut | H | 1-Pyrrolyl | H | CH$_2$—N | NH | —(CH$_2$)$_3$— |
| 49 | CH$_3$ | NH$_2$ | H | iProp | H | 2-Napht | H | CH=C | —CH$_2$— | —(CH$_2$)$_3$— |
| 50 | CH$_3$ | NH$_2$ | H | Et | H | tBut | H | CH$_2$—N | S | —(CH$_2$)$_3$— |
| 51 | CH$_3$ | NH$_2$ | OMe | tBut | H | H | H | CH=C | —CH$_2$— | —(CH$_2$)$_3$— |
| 52 | CH$_3$ | NH$_2$ | OMe | CF$_3$ | H | H | H | CH=C | S | —(CH$_2$)$_3$— |
| 53 | CH$_3$ | NH$_2$ | H | CF$_3$ | H | tBut | H | CH$_2$—N | NH | —(CH$_2$)$_3$— |
| 54 | CH$_3$ | NH$_2$ | OiProp | iProp | H | H | H | CH$_2$—N | S | —(CH$_2$)$_3$— |
| 55 | CH$_3$ | NH$_2$ | H | H | CN | tBut | H | CH$_2$—N | O | —(CH$_2$)$_3$— |
| 56 | CH$_3$ | NH$_2$ | H | H | F | tBut | H | CH=C | S | —(CH$_2$)$_3$— |
| 57 | CH$_3$ | NH$_2$ | H | H | Cl | iProp | H | CH$_2$—N | —CH$_2$— | —(CH$_2$)$_3$— |
| 58 | CH$_3$ | NH$_2$ | H | tBut | H | H | OMe | CH$_2$—N | S | —(CH$_2$)$_3$— |
| 59 | CH$_3$ | NH$_2$ | OMe | tBut | H | tBut | H | CH$_2$—N | S | —(CH$_2$)$_3$— |
| 60 | CH$_3$ | NH$_2$ | OMe | tBut | H | CF$_3$ | H | CH$_2$—N | S | —(CH$_2$)$_3$— |
| 61 | CH$_3$ | NH$_2$ | OMe | CF$_3$ | H | tBut | H | CH$_2$—N | NH | —(CH$_2$)$_3$— |
| 62 | CH$_3$ | NH$_2$ | H | nProp | CN | tBut | H | CH=C | —CH$_2$— | —(CH$_2$)$_3$— |
| 63 | CH$_3$ | NH$_2$ | H | CF$_3$ | CN | iProp | H | CH$_2$—N | S | —(CH$_2$)$_3$— |
| 64 | CH$_3$ | NH$_2$ | H | Ph | C≡CH | tBut | H | CH=C | —CH$_2$— | —(CH$_2$)$_3$— |
| 65 | CH$_3$ | NH$_2$ | OMe | tBut | CN | H | H | CH=C | S | —(CH$_2$)$_3$— |
| 66 | CH$_3$ | NH$_2$ | H | tBut | CN | CF$_3$ | OMe | CH$_2$—N | NH | —(CH$_2$)$_3$— |
| 67 | CH$_3$ | NH$_2$ | OMe | nProp | F | tBut | H | CH$_2$—N | S | —(CH$_2$)$_3$— |
| 68 | CH$_3$ | NH$_2$ | H | Ph | CN | tBut | Me | CH$_2$—N | O | —(CH$_2$)$_3$— |
| 69 | CH$_3$ | NH$_2$ | OMe | tBut | F | H | H | CH=C | S | —(CH$_2$)$_3$— |
| 70 | CH$_3$ | NH$_2$ | H | iProp | H | H | OMe | CH$_2$—N | S | —(CH$_2$)$_3$— |
| 71 | iProp | NH$_2$ | H | tBut | H | Me | H | CH$_2$—N | S | —(CH$_2$)$_3$— |

TABLE 4-continued

| Example No. | R1 | R2 | R5 | R6 | R7 | R8 | R9 | X—Y | A¹ | A² |
|---|---|---|---|---|---|---|---|---|---|---|
| 72 | iProp | NH₂ | H | tBut | H | Ph | H | CH₂—N | NH | —(CH₂)₄— |
| 73 | iProp | NH₂ | H | tBut | H | 1-Pyrrolyl | H | CH₂—N | S | —(CH₂)₄— |
| 74 | iProp | NH₂ | H | iProp | H | 2-Napht | H | CH₂—N | —CH₂— | —(CH₂)₃— |
| 75 | iProp | NH₂ | H | Et | H | tBut | H | CH₂—N | S | —(CH₂)₅— |
| 76 | iProp | NH₂ | OMe | tBut | H | H | H | CH₂—N | O | —(CH₂)₅— |
| 77 | iProp | NH₂ | OMe | CF₃ | H | H | H | CH=C | NH | —(CH₂)₄— |
| 78 | iProp | NH₂ | H | CF₃ | H | tBut | H | CH₂—N | —CH₂— | —(CH₂)₄— |
| 79 | iProp | NH₂ | OiProp | iProp | H | H | H | CH=C | S | —(CH₂)₃— |
| 80 | iProp | NH₂ | H | H | CN | tBut | H | CH₂—N | NH | —(CH₂)₃— |
| 81 | iProp | NH₂ | H | H | F | tBut | H | CH₂—N | S | —(CH₂)₃— |
| 82 | iProp | NH₂ | H | H | Cl | iProp | H | CH=C | —CH₂— | —(CH₂)₃— |
| 83 | iProp | NH₂ | H | tBut | H | H | OMe | CH₂—N | S | —(CH₂)₃— |
| 84 | iProp | NH₂ | OMe | tBut | H | tBut | H | CH₂—N | S | —(CH₂)₄— |
| 85 | iProp | NH₂ | OMe | tBut | H | CF₃ | H | CH₂—N | S | —(CH₂)₃— |
| 86 | iProp | NH₂ | OMe | CF₃ | H | tBut | H | CH₂—N | NH | —(CH₂)₅— |
| 87 | iProp | NH₂ | H | nProp | CN | tBut | H | CH=C | —CH₂— | —(CH₂)₃— |
| 88 | iProp | NH₂ | H | CF₃ | CN | iProp | H | CH₂—N | S | —(CH₂)₄— |
| 89 | iProp | NH₂ | H | Ph | C=CH | tBut | H | CH=C | —CH₂— | —(CH₂)₃— |
| 90 | iProp | NH₂ | OMe | tBut | CN | H | H | CH=C | S | —(CH₂)₆— |
| 91 | iProp | NH₂ | H | tBut | CN | CF₃ | OMe | CH₂—N | NH | —(CH₂)₃— |
| 92 | iProp | NH₂ | OMe | nProp | F | tBut | H | CH₂—N | S | —(CH₂)₅— |
| 93 | iProp | NH₂ | H | Ph | CN | tBut | Me | CH₂—N | O | —(CH₂)₃— |
| 94 | iProp | NH₂ | OMe | tBut | F | H | H | CH=C | S | —(CH₂)₄— |
| 95 | iProp | NH₂ | H | iProp | H | H | OMe | CH₂—N | S | —(CH₂)₃— |
| 96 | iProp | NHMe | H | tBut | H | Me | H | CH₂—N | S | —CH₂—CH=CH—CH₂— |
| 97 | iProp | NHMe | H | tBut | H | Ph | H | CH₂—N | —CH₂— | —CH₂—CH=CH—CH₂— |
| 98 | iProp | NHMe | H | tBut | H | 1-Pyrrolyl | H | CH₂—N | S | —CH₂—CH=CH—CH₂— |
| 99 | iProp | NHMe | H | iProp | H | 2-Napht | H | CH₂—N | NH | —CH₂—C(CH₃)=CH—CH₂— |
| 100 | iProp | NHMe | H | Et | H | tBut | H | CH₂—N | S | —CH₂—C(CH₃)=CH—CH₂— |
| 101 | iProp | OH | OMe | tBut | H | H | H | CH₂—N | —CH₂— | —CH₂—C(CH₃)=CH—CH₂— |
| 102 | iProp | OH | OMe | CF₃ | H | H | H | CH₂—N | NH | —CH₂—C(CH₃)=CH—CH₂— |
| 103 | iProp | OH | H | CF₃ | H | tBut | H | CH₂—N | S | —CH₂—CH=CH—CH₂— |
| 104 | iProp | OH | OiProp | iProp | H | H | H | CH=C | —CH₂— | —CH₂—CH=CH—CH₂— |
| 105 | iProp | OMe | H | H | CN | tBut | H | CH=C | —CH₂— | —CH₂—CH=CH—CH₂— |
| 106 | iProp | OMe | H | H | F | tBut | H | CH=C | S | —CH₂—C(CH₃)=CH—CH₂— |
| 107 | iProp | OMe | H | H | Cl | iProp | H | CH=C | O | —CH₂—C(CH₃)=CH—CH₂— |
| 108 | iProp | OMe | H | tBut | H | H | OMe | CH=C | NH | —CH₂—C(CH₃)=CH—CH₂— |
| 109 | iProp | NHMe | OMe | tBut | H | tBut | H | CH₂—N | S | —CH₂—CH=CH—CH₂— |
| 110 | iProp | NHMe | OMe | tBut | H | CF₃ | H | CH₂—N | —CH₂— | —CH₂—CH=CH—CH₂— |
| 111 | iProp | NHMe | OMe | CF₃ | H | tBut | H | CH₂—N | S | —CH₂—CH=CH—CH₂— |
| 112 | iProp | NHMe | H | nProp | CN | tBut | H | CH₂—N | NH | —CH₂—C(CH₃)=CH—CH₂— |
| 113 | iProp | NHMe | H | CF₃ | CN | iProp | H | CH₂—N | S | —CH₂—C(CH₃)=CH—CH₂— |
| 114 | iProp | OH | H | Ph | C=CH | tBut | H | CH₂—N | —CH₂— | —CH₂—C(CH₃)=CH—CH₂— |
| 115 | iProp | OH | OMe | tBut | CN | H | H | CH₂—N | NH | —CH₂—C(CH₃)=CH—CH₂— |
| 116 | iProp | OH | H | tBut | CN | CF₃ | OMe | CH₂—N | S | —CH₂—CH=CH—CH₂— |
| 117 | iProp | OH | OMe | nProp | F | tBut | H | CH=C | —CH₂— | —CH₂—CH=CH—CH₂— |
| 118 | iProp | OMe | H | Ph | CN | tBut | Me | CH=C | —CH₂— | —CH₂—CH=CH—CH₂— |
| 119 | iProp | OMe | OMe | tBut | F | H | H | CH=C | S | —CH₂—C(CH₃)=CH—CH₂— |
| 120 | iProp | OMe | H | iProp | H | H | OMe | CH=C | S | —CH₂—C(CH₃)=CH—CH₂— |

TABLE 5

| Example No. | R1 | R2 | R6 | R8 | R9 | X—Y | A¹ | A² |
|---|---|---|---|---|---|---|---|---|
| 121 | CH₃ | NH₂ | tBut | Ph | H | CH₂—N | —CH₂— | —(CH₂)₃— |

TABLE 5-continued

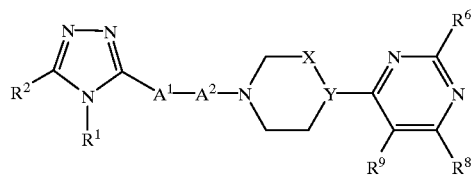

| Example No. | R1 | R2 | R6 | R8 | R9 | X—Y | A¹ | A² |
|---|---|---|---|---|---|---|---|---|
| 122 | CH₃ | NH₂ | tBut | 2-Napht | H | CH₂—N | S | —CH₂—C(CH₃)=CH—CH₂— |
| 123 | CH₃ | NH₂ | tBut | 1-Pyrrolyl | H | CH₂—N | S | —(CH₂)₃— |
| 124 | CH₃ | NHMe | tBut | cHex | H | CH=C | —CH₂— | —(CH₂)₃— |
| 125 | CH₃ | NH₂ | tBut | nHex | H | CH₂—N | S | —(CH₂)₅— |
| 126 | CH₃ | NH₂ | tBut | H | OMe | CH₂—N | —CH₂— | —(CH₂)₃— |
| 127 | CH₃ | NHMe | iProp | H | OMe | CH₂—N | S | —CH₂—C(CH₃)=CH—CH₂— |
| 128 | CH₃ | NH₂ | H | CH₃ | OMe | CH=C | NH | —(CH₂)₃— |
| 129 | CH₃ | NH₂ | H | iProp | OMe | CH₂—N | O | —CH₂—CH=CH—CH₂— |
| 130 | CH₃ | NH₂ | tBut | tBut | OMe | CH₂—N | —CH₂— | —(CH₂)₃— |
| 131 | CH₃ | NHMe | tBut | iProp | OMe | CH₂—N | S | —CH₂—C(CH₃)=CH—CH₂— |
| 132 | CH₃ | NH₂ | Ph | tBut | Cl | CH₂—N | S | —(CH₂)₄— |
| 133 | CH₃ | NH₂ | 2-Napht | tBut | Me | CH=C | —CH₂— | —(CH₂)₃— |
| 134 | CH₃ | NH₂ | tBut | CF₃ | OMe | CH₂—N | S | —(CH₂)₃— |
| 135 | CH₃ | NH₂ | tBut | H | CH₃ | CH₂—N | S | —(CH₂)₃— |
| 136 | iProp | NH₂ | tBut | Ph | H | CH₂—N | S | —(CH₂)₃— |
| 137 | iProp | NH₂ | tBut | 2-Napht | H | CH=C | NH | —(CH₂)₃— |
| 138 | iProp | NH₂ | tBut | 1-Pyrrolyl | H | CH₂—N | O | —CH₂—C(CH₃)=CH—CH₂— |
| 139 | iProp | NH₂ | tBut | cHex | H | CH₂—N | —CH₂— | —(CH₂)₃— |
| 140 | iProp | OH | tBut | nHex | H | CH₂—N | S | —(CH₂)₄— |
| 141 | nProp | OH | tBut | H | OMe | CH=C | S | —(CH₂)₄— |
| 142 | nProp | OMe | iProp | H | OMe | CH₂—N | —CH₂— | —CH₂—CH=CH—CH₂— |
| 143 | nProp | OMe | H | CH₃ | OMe | CH₂—N | —CH₂— | —(CH₂)₃— |
| 144 | nProp | NCH₂Ph | H | iProp | OMe | CH₂—N | S | —CH₂—C(CH₃)=CH—CH₂— |
| 145 | iProp | OH | tBut | tBut | OMe | CH₂—N | —CH₂— | —(CH₂)₄— |
| 146 | iProp | OH | tBut | iProp | OMe | CH₂—N | S | —CH₂—CH=CH—CH₂— |
| 147 | iProp | OMe | Ph | tBut | Cl | CH₂—N | S | —(CH₂)₅— |
| 148 | nProp | OMe | 2-Napht | tBut | Me | CH=C | —CH₂— | —(CH₂)₃— |
| 149 | nProp | NCH₂Ph | tBut | CF₃ | OMe | CH₂—N | S | —(CH₂)₄— |
| 150 | nProp | NHMe | tBut | H | CH₃ | CH=C | S | —(CH₂)₃— |

TABLE 6

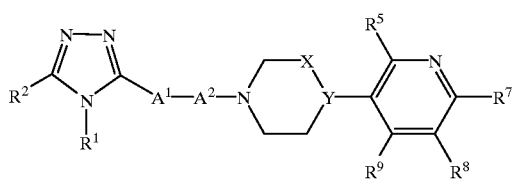

| Example No. | R1 | R2 | R5 | R7 | R8 | R9 | X—Y | A | B |
|---|---|---|---|---|---|---|---|---|---|
| 151 | CH₃ | NH₂ | OMe | H | tBut | H | CH₂—N | S | —(CH₂)₃— |
| 152 | CH₃ | OH | OMe | H | CF₃ | H | CH₂—N | S | —(CH₂)₃— |
| 153 | iProp | NHMe | OMe | H | tBut | H | CH₂—N | NH | —CH₂—CH=CH—CH₂— |
| 154 | CH₃ | NH₂ | H | CN | tBut | H | CH=C | —CH₂— | —CH₂—C(CH₃)=CH—CH₂— |
| 155 | CH₃ | NHMe | H | F | tBut | H | CH₂—N | S | —(CH₂)₃— |
| 156 | cProp | NH₂ | Me | Cl | iProp | H | CH=C | —CH₂— | —(CH₂)₃— |
| 157 | CH₃ | NHMe | H | H | iProp | OMe | CH=C | S | —(CH₂)₃— |
| 158 | CH₃ | NH₂ | H | H | tBut | OMe | CH₂—N | NH | —CH₂—CH=CH—CH₂— |
| 159 | iProp | NH₂ | CN | H | CF₃ | H | CH₂—N | S | —(CH₂)₄— |
| 160 | OH | NHMe | H | CN | H | OMe | CH₂—N | O | —(CH₂)₃— |
| 161 | CH₃ | OH | H | H | tBu | OEt | CH=C | S | —CH₂—C(CH₃)=CH—CH₂— |
| 162 | Et | NH₂ | H | CN | tBut | H | CH₂—N | —CH₂— | —(CH₂)₃— |
| 163 | CH₃ | NH₂ | Me | H | iProp | H | CH₂—N | S | —(CH₂)₃— |
| 164 | iProp | NH₂ | OMe | CN | tBut | H | CH₂—N | S | —(CH₂)₄— |
| 165 | CH₃ | NH₂ | OMe | Me | tBut | H | CH₂—N | S | —(CH₂)₃— |
| 166 | CH₃ | NHMe | H | CN | tBut | OMe | CH₂—N | NH | —CH₂—CH=CH—CH₂— |
| 167 | CH₃ | NH₂ | Me | H | tBut | OMe | CH=C | —CH₂— | —CH₂—C(CH₃)=CH—CH₂— |
| 168 | iProp | NH₂ | H | Cl | CF₃ | Me | CH₂—N | S | —(CH₂)₅— |
| 169 | OH | NHMe | OMe | CN | tBut | Me | CH=C | S | —(CH₂)₃— |
| 170 | CH₃ | OH | Me | Me | iProp | Me | CH=C | S | —(CH₂)₄— |

TABLE 6-continued

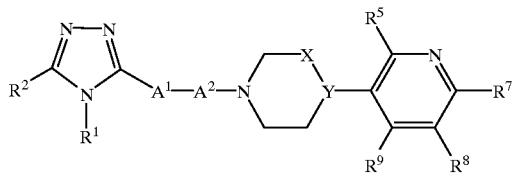

| Example No. | R1 | R2 | R5 | R7 | R8 | R9 | X—Y | A | B |
|---|---|---|---|---|---|---|---|---|---|
| 171 | CH₃ | OH | OMe | H | iProp | H | CH₂—N | S | —(CH₂)₃— |

TABLE 7

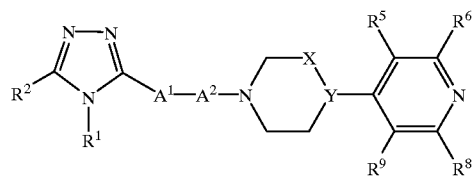

| Example No. | R1 | R2 | R5 | R6 | R8 | R9 | X—Y | A¹ | A² |
|---|---|---|---|---|---|---|---|---|---|
| 172 | CH₃ | NH₂ | H | tBut | tBut | H | CH₂—N | S | —(CH₂)₃— |
| 173 | CH₃ | OH | H | tBut | Ph | H | CH₂—N | S | —(CH₂)₃— |
| 174 | iProp | NHMe | H | tBut | 1-Pyrrolyl | H | CH₂—N | NH | —CH₂—CH=CH—CH₂— |
| 175 | CH₃ | NH₂ | H | nPropyl | tBut | H | CH=C | —CH₂— | —CH₂—C(CH₃)=CH—CH₂— |
| 176 | CH₃ | NHMe | H | CF₃ | tBut | H | CH₂—N | S | —(CH₂)₃— |
| 177 | cProp | NH₂ | H | 2-Napht | tBut | H | CH=C | —CH₂— | —(CH₂)₃— |
| 178 | CH₃ | NHMe | OMe | tBut | H | H | CH=C | S | —(CH₂)₃— |
| 179 | CH₃ | NH₂ | OMe | iProp | H | H | CH₂—N | NH | —CH₂—CH=CH—CH₂— |
| 180 | iProp | NH₂ | OMe | H | CF₃ | H | CH₂—N | S | —(CH₂)₄— |
| 181 | OH | NHMe | H | tBut | H | OMe | CH₂—N | O | —(CH₂)₃— |
| 182 | CH₃ | OH | H | iProp | H | Me | CH=C | S | —CH₂—C(CH₃)=CH—CH₂— |
| 183 | Et | NH₂ | CN | tBut | H | H | CH₂—N | —CH₂— | —(CH₂)₃— |
| 184 | CH₃ | NH₂ | H | H | CF₃ | Me | CH₂—N | S | —(CH₂)₃— |
| 185 | OH | NHMe | OMe | tBut | iProp | H | CH₂—N | S | —(CH₂)₄— |
| 186 | CH₃ | OH | OMe | CF₃ | tBut | H | CH₂—N | NH | —CH₂—CH=CH—CH₂— |
| 187 | Et | NH₂ | Me | tBut | nProp | H | CH=C | —CH₂— | —CH₂—C(CH₃)=CH—CH₂— |
| 188 | CH₃ | NH₂ | Me | tBut | H | OMe | CH₂—N | S | —(CH₂)₅— |
| 189 | CH₃ | NH₂ | OMe | tBut | tBut | OMe | CH=C | —CH₂— | —(CH₂)₃— |
| 190 | iProp | NH₂ | Me | CF₃ | tBut | OMe | CH=C | S | —(CH₂)₄— |
| 191 | CH₃ | OH | H | nProp | tBut | H | CH₂—N | S | —(CH₂)₃— |

TABLE 8

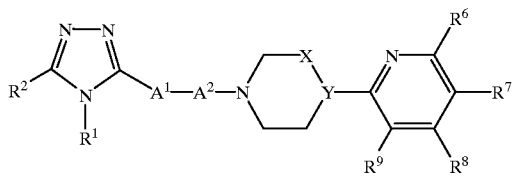

| Example No. | R1 | R2 | R6 | R7 | R8 | R9 | X—Y | A¹ | A² |
|---|---|---|---|---|---|---|---|---|---|
| 192 | CH₃ | NH₂ | tBut | H | tBut | H | CH₂—N | S | —(CH₂)₃— |
| 193 | CH₃ | OH | tBut | CN | H | H | CH₂—N | S | —(CH₂)₃— |
| 194 | iProp | NHMe | tBut | H | H | OMe | CH₂—N | NH | —CH₂—CH=CH—CH₂— |
| 195 | CH₃ | NH₂ | H | CN | tBu | H | CH=C | —CH₂— | —CH₂—C(CH₃)=CH—CH₂— |
| 196 | CH₃ | NHMe | CF₃ | H | tBut | H | CH₂—N | S | —(CH₂)₃— |
| 197 | cProp | NH₂ | nProp | H | iProp | H | CH=C | —CH₂— | —(CH₂)₃— |
| 198 | CH₃ | NHMe | H | H | iProp | OMe | CH=C | S | —(CH₂)₃— |
| 199 | CH₃ | NH₂ | tBut | H | tBut | H | CH₂—N | NH | —CH₂—CH=CH—CH₂— |
| 200 | iProp | NH₂ | tBut | CN | H | H | CH₂—N | S | —(CH₂)₄— |
| 201 | OH | NHMe | tBut | H | H | OMe | CH₂—N | O | —(CH₂)₃— |
| 202 | CH₃ | OH | H | CN | tBu | H | CH=C | S | —CH₂—C(CH₃)=CH—CH₂— |
| 203 | Et | NH₂ | CF₃ | H | tBut | H | CH₂—N | —CH₂— | —(CH₂)₃— |

TABLE 8-continued

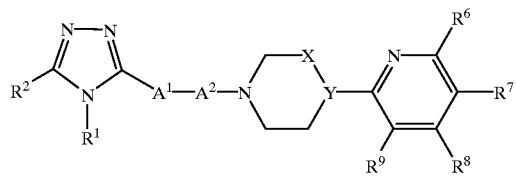

| Example No. | R1 | R2 | R6 | R7 | R8 | R9 | X—Y | A¹ | A² |
|---|---|---|---|---|---|---|---|---|---|
| 204 | CH₃ | NH₂ | nProp | H | iProp | H | CH₂—N | S | —(CH₂)₃— |
| 205 | CH₃ | NH₂ | nProp | CN | tBut | H | CH₂—N | S | —(CH₂)₄— |
| 206 | CH₃ | OH | CF₃ | CN | iProp | H | CH₂—N | S | —(CH₂)₃— |
| 207 | iProp | NHMe | Ph | C≡CH | tBut | H | CH₂—N | NH | —CH₂—CH=CH—CH₂— |
| 208 | CH₃ | NH₂ | tBut | CN | tBut | H | CH=C | —CH₂— | —CH₂—C(CH₃)=CH—CH₂— |
| 209 | CH₃ | NHMe | tBut | H | nProp | OMe | CH₂—N | S | —(CH₂)₃— |
| 210 | cProp | NH₂ | Ph | H | tBut | OMe | CH=C | —CH₂— | —(CH₂)₅— |
| 211 | CH₃ | NHMe | CF₃ | H | tBut | OMe | CH=C | S | —(CH₂)₃— |
| 212 | CH₃ | NH₂ | tBut | F | H | Me | CH₂—N | NH | —CH₂—CH=CH—CH₂— |
| 213 | iProp | NH₂ | nProp | CN | tBut | Me | CH₂—N | S | —CH₂—CH=CH—CH₂— |
| 214 | CH₃ | OH | nProp | C≡CH | tBut | OMe | CH=C | —CH₂— | —CH₂—C(CH₃)=CH—CH₂— |
| 215 | iProp | NHMe | tBut | CN | H | OMe | CH₂—N | S | —(CH₂)₄— |
| 216 | CH₃ | OH | H | H | iProp | OMe | CH₂—N | S | —(CH₂)₃— |

Examples of Pharmaceutical Forms
A) Tablets
Tablets of the following composition are compressed in a tabletting machine in a conventional manner:
40 mg of substance of Example 1
120 mg of corn starch
13.5 mg of gelatin
45 mg of lactose
2.25 mg of Aerosil® (chemically pure silica in submicroscopically fine dispersion)
6.75 mg of potato starch (as 6% strength paste)
B) Sugar-coated Tablets
20 mg of substance of Example 4
60 mg of core composition
70 mg of sugar-coating composition The core composition comprises 9 parts of corn starch, 3 parts of lactose and 1 part of vinylpyrrolidone/vinyl acetate 60:40 copolymer. The sugar-coating composition comprises 5 parts of sucrose, corn starch, 2 parts of calcium carbonate and 1 part talc. The sugar coated tablets produced in this way are subsequently provided with an enteric coating.

Biological Investigations—Receptor-binding Studies
1) $D_3$ Binding Assay

Cloned human $D_3$ receptor-expressing CCL 1.3 mouse fibroblasts obtained from Res. Biochemicals Internat. One Strathmore Rd., Natick, Mass. 01760-2418 USA, were used for the binding studies.

Cell Preparation

The $D_3$-expressing cells where grown in RPMI-1640 containing 10% fetal calf serum (GIBCO No. 041-32400 N); 100 U/ml penicillin and 0.2% streptomycin (GIBCO BRL, Gaithersburg, Md., USA). After 48h, the cells were washed with PBS and incubated with 0.05% trypsin-containing PBS for 5 min. Neutralization with medium was then carried out, and the cells were collected by centrifugation at 300×g. To lyze the cells, the pellet was briefly washed with lysis buffer (5 mM tris-HCl, pH 7.4, with 10% glycerol) and then incubated in a concentration of 10⁷ cells/ml of lysis buffer at 4° C. for 30 min. The cells were centrifuged at 200×g for 10 min and the pellet was stored in liquid nitrogen.

Binding Assays

For the $D_3$ receptor binding assay, the membranes were suspended in incubation buffer (50 mM tris-HCl, pH 7.4, with 120 nM NaCl, 5 mM KCl, 2 mM $CaCl_2$, 2 mM $MgCl_2$, 10 μM quinolinol, 0.1% ascorbic acid and 0.1% BSA) in a concentration of about 10⁶ cells/250 μl of assay mixture and incubated at 30° C. with 0.1 nM ¹²⁵iodosulpiride in the presence and absence of test substance. The non-specific binding was determines using 10⁻⁶ M spiperone.

After 60 min, the free and the bound radioligand was separated by filtration through GF/B glasd fiber filters (Whatman, England) on a Skatron cell collector (Skatron, Lier, Norway), and the filters were washed with ice-cold tris-HCl buffer, pH 7.4. The radioactivity collected on the filters was quantified using a Packard 2200 CA ligand scintillation counter.

The $K_i$ values were determined by non-linear regression analysis using the LIGAND program.

2) $D_2$ Binding Assay
Membrane Preparation
a) Nucleus Caudatus (Bovine)

Nucleus caudatus was removed from bovine brain and washed with ice-cold 0.32 M sucrose solution. After determination of the weight, the material was committed and homogenized in 5–10 volumes of sucrose solution using a Potter-Evehjem homogenizer (500 rpm). The homogenate was centrifuged at 3,000×g for 15 minutes (4° C.), and the resulting supernatant was subjected to another 15-minute centrifugation at 40,000×g. The residue was then washed twice, by resuspension and centrifugation, with 50 mM tris-HCl, pH 7.4. The membranes were were stored in liquid nitrogen until used.

b) Striatum (Rat)

Striati from Sprague-Dawley rats were washed in ice-cold 0.32 M sucrose solution. After determination of the weight, the parts of the brain were homogenized in 5–10 volumes of sucrose solution using a Potter-Elvehjem homogenizer (500 rpm). The homogenate was centrifuged at 40,000×g for 10 minutes (4° C.), and then the residue was washed several times, by resuspension and centrifugation, with 50 mM tris-HCl, 0.1 mM EDTA and 0.01% ascorbic acid (pH 7.4). The washed residue was resuspended in the abovementioned buffer and incubated at 37° C. for 20 minutes (to break down the endogenous dopamine). The membranes were then washed twice with buffer and portions were frozen in liquid nitrogen. The membrane preparation was stable for a maximum of one week.

Binding Assay a) ³H-Spiperone ($D_{2low}$)

Nucleus caudatus membranes were taken up in incubation buffer (mM: tris-HCl 50, NaCl 120, KCl 5, $MgCl_2$ 1, $CaCl_2$ 2, pH 7.4). Various mixtures, each of 1 ml, were prepared:

Total binding: 400 μg of membranes+0.2 nmol/l ³H-spiperone (Du Pont de Nemours, NET-565)

Non-specific binding: as mixtures for total binding+10 μM (+)-butaclamol.

Test substance: as mixtures for total binding+increasing concentrations of test substance.

After incubation at 25° C. for 60 minutes, the mixtures were filtered through GF/B glass fibre filters (Whatman, England) on a Skatron cell collector (from Zinsser, Frankfurt), and the filters were wshed with ice-cold 50 mM tris-KCl buffer, pH 7.4. The radioactivity collected on the filters was quantified using a Packard 2200 CA liquid scintillation counter.

The $K_i$ values were determined by non-linear regression analysis using the LIGAND program or by conversion of the $IC_{50}$ values using the formula of Cheng and Prusoff.

b) ³H-ADTN ($D_{2high}$)

Striatum membranes were taken up in incubation buffer (50 mM tris-HCl, pH 7.4, 1 mM $MnCl_2$ and 0.1% ascorbic acid).

Various mixtures, each of 1 ml, were prepared.

Total binding: 300 μg wet weight+1 nM ³H-ADTN (Du Pont de Nemours, customer synthesis)+100 nM SCH 23390 (occupation of D1 receptors).

Non-specific binding: as mixtures for total binding+50 nM spiperone.

Test substance: as mixtures for total binding+increasing concentrations of test substance.

After incubation at 25° C. for 60 minutes, the nmixtures were filtered through GF/B glass fibre filters (Whatman, England) on a Skatron cell collector (from Zinsser, Frankfurt), and the filters were wshed with ice-cold 50 mM tris-HCl buffer, pH 7.4. The radioactivity collected on the filters was quantified using a Packard 2200 CA liquid scintillation counter.

The evaluation took place as under a).

In these assays, the compounds according to the invention show very good affinities and high selectivities for the $D_3$ receptor. The results obtained for representative compounds are compiled in the following Table 9.

TABLE 9

| | Receptor binding | | |
|---|---|---|---|
| Example No. | $D_3$ ¹²⁵I-sulpiride $K_i$ [nM] | $D_2$ ³H-spiperone $K_i$ [mM] | Selectivity $K_iD_2/K_iD_3$ |
| 10 | 4.5 | 219 | 49 |
| 15 | 8.8 | 517 | 58 |
| 24 | 1.8 | 120 | 67 |
| 41 | 8.1 | 1,500 | 185 |
| 42 | 13.4 | 2,450 | 182 |
| 37 | 1.7 | 300 | 176 |

For comparison, the compound of the formula

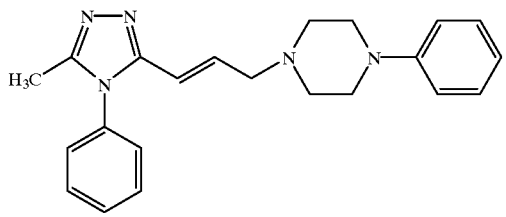

(U.S. Pat. No. 4,577,020; Example 3) was subjected to the above $D_3$ binding assay. A $K_i$ of 4100 [nM] was found; ie. the compound-has virtually no affinity for the $D_3$ receptor.

We claim:

1. A triazole compound of formula I

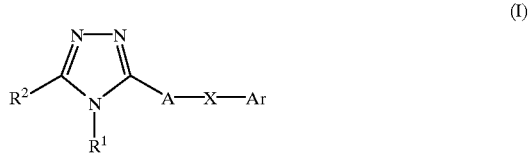

(I)

wherein

A is a straight-chain or branched $C_1$–$C_{18}$-alkylene group, or a straight chain or branched group consisting of 1 to 18 methylene members and one or two members selected from the group consisting of O, S, $NR^3$, $NR^3CO$, COO, OCO, $C_3$–$C_6$-cycloalkylene, a double bond and a triple bond, X is

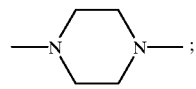

$R^1$ is H, $CO_2R^3$, $NR^3R^4$, $OR^4$, $C_3$–$C_6$-cycloalkyl or $C_1$–$C_8$-alkyl which is unsubstituted or substituted by OH, $OC_1$–$C_8$-alkyl or halogen;

$R^2$ has the meanings indicated for $R^1$ or is $CF_3$, $SR^3$, halogen or CN;

$R^3$ is H or $C_1$–$C_8$-alkyl which is unsubstituted or substituted by OH, $OC_1$–$C_8$-alkyl, phenyl or halogen;

$R^4$ has the meanings indicated for $R^3$ or is $COR^3$ or $CO_2R^3$;

Ar is an optionally fused phenyl ring selected from the group consisting of phenyl, naphthalene, dihydronaphthalene, tetrahydronaphthalene, quinoline, dihydroquinoline, tetrahydroquinoline, indole, dihydroindole, benzimidazole, benzothiazole, benzothiadiazole, benzopyrrole and benzotriazole, and which optionally fused phenyl ring is unsubstituted or carries from one to four substituents selected from the group consisting of: $OR^4$, $C_1$–$C_8$-alkyl, $C_2$–$C_6$-alkenyl, $C_2$–$C_6$-alkynyl, halogen, CN, $CO_2R^3$, $NO_2$, $SO_2R^3$, $SO_3R^3$, $NR^3R^4$, $SO_2NR^3R^4$, $SR^3$, $CF_3$, $CHF_2$, $C_3$–$C_6$-cycloalkyl, phenyl, naphthalene, pyrrolidine, piperidine, morpholine, piperazine, pyridine, pyrimidine, triazine, pyrrole, thiophene, thiazole, imidazole, oxazole, isoxazole, pyrazole and thiadiazole, wherein each of the cyclic substituents is unsubstituted or substituted by $C_1$–$C_8$-alkyl, halogen, $OC_1$–$C_8$-alkyl, OH, $NO_2$ or $CF_3$, or a salt thereof with a physiologically tolerated acid.

2. The compound of formula I defined in claim 1, wherein the optionally fused phenyl ring is selected from the group consisting of phenyl, naphthalene, dihydronaphthalene, tetrahydronaphthalene, quinoline, dihydroquinoline, tetrahydroquinoline, indole, dihydroindole and benzothiazole.

3. The compound of formula I defined in claim 1, wherein the optionally fused phenyl ring is unsubstituted or carries from one to four substituents selected from the group consisting of: $OR^4$, $C_1$–$C_8$-alkyl, $C_2$–$C_6$-alkenyl, $C_2$–$C_6$-alkynyl, halogen, CN, $CO_2R^3$, $NO_2$, $SO_2R^3$, $SO_3R^3$, $NR^3R^4$, $SO_2NR^3R^4$, $SR^3$, $CF_3$, $CHF_2$, $C_3$–$C_6$-cycloalkyl, phenyl, naphthalene, pyrrolidine, piperidine, morpholine, pyrrole, thiophene and imidazole.

4. The compound of formula I defined in claim 1, wherein the optionally fused phenyl ring is selected from the group consisting of phenyl, naphthalene, dihydronaphthalene, tetrahydronaphthalene, quinoline, dihydroquinoline, tetrahydroquinoline, indole, dihydroindole and benzothiazole, and which optionally fused phenyl ring is unsubstituted or carries from one to four substituents selected from the group consisting of: $OR^4$, $C_1$–$C_8$-alkyl, $C_2$–$C_6$-alkenyl, $C_2$–$C_6$-alkynyl, halogen, CN, $CO_2R^3$, $NO_2$, $SO_2R^3$, $SO_3R^3$, $NR^3R^4$, $SO_2NR^3R^4$, $SR^3$, $CF_3$, $CHF_2$, $C_3$–$C_6$-cycloalkyl, phenyl, naphthalene, pyrrolidine, piperidine, morpholine, pyrrole, thiophene and imidazole, wherein each of the cyclic substituents is unsubstituted or substituted by $C_1$–$C_8$-alkyl, halogen, $OC_1$–$C_8$-alkyl, OH, $NO_2$ or $CF_3$.

5. The compound of formula I defined in claim 1, wherein the optionally fused phenyl ring Ar is selected from the group consisting of phenyl, naphthalene, dihydronaphthalene and tetrahydronaphthalene, and which optionally fused phenyl ring is unsubstituted or carries from one to four substituents selected from the group consisting of: $OR^4$, $C_1$–$C_8$-alkyl, $C_2$–$C_6$-alkenyl, $C_2$–$C_6$-alkynyl, halogen, CN, $CO_2R^3$, $NO_2$, $SO_2R^3$, $SO_3R^3$, $NR^3R^4$, $SO_2NR^3R^4$, $SR^3$, $CF_3$, $CHF_2$, $C_3$–$C_6$-cycloalkyl, phenyl, naphthalene, pyrrolidine, piperidine, morpholine, piperazine, pyridine, pyrimidine, triazine, pyrrole, thiophene, thiazole, imidazole, oxazole, isoxazole, pyrazole and thiadiazole, wherein each of the cyclic substituents is unsubstituted or substituted by $C_1$–$C_8$-alkyl, halogen, $OC_1$–$C_8$-alkyl, OH, $NO_2$ or $CF_3$.

6. The compound of formula I defined in claim 1, wherein Ar is a phenyl ring which is unsubstituted or substituted by from one to four substituents selected from the group consisting of: $OR^4$, $C_1$–$C_8$-alkyl, $C_2$–$C_6$-alkenyl, $C_2$–$C_6$-alkynyl, halogen, CN, $CO_2R^3$, $NO_2$, $SO_2R^3$, $SO_3R^3$, $NR^3R^4$, $SO_2NR^3R^4$, $SR^3$, $CF_3$, $CHF_2$, $C_3$–$C_6$-cycloalkyl, phenyl, naphthalene, pyrrolidine, piperidine, morpholine, piperazine, pyridine, pyrimidine, triazine, pyrrole, thiophene, thiazole, imidazole, oxazole, isoxazole, pyrazole and thiadiazole, wherein each of the cyclic substituents is unsubstituted or substituted by $C_1$–$C_8$-alkyl, halogen, $OC_1$–$C_8$-alkyl, OH, $NO_2$ or $CF_3$.

7. The compound of formula I defined in claim 1 wherein
$R^1$ is H, $CO_2R^3$, $NR^3R^4$, $OR^4$ or $C_1$–$C_8$-alkyl which is unsubstituted or substituted by OH, $OC_1$–$C_8$-alkyl or halogen;
$R^3$ is H or $C_1$–$C_8$-alkyl which is unsubstituted or substituted by OH, $OC_1$–$C_8$-alkyl or halogen; and
wherein the optionally fused phenyl ring is unsubstituted or carries one or two substituents selected from the group consisting of: $OR^4$, $C_1$–$C_8$-alkyl, halogen, CN, $CO_2R^3$, $NO_2$, $SO_2R^3$, $SO_3R^3$, $NR^3R^4$, $SO_2NR^3R^4$, $SR^3$, $CF_3$, $CHF_2$, $C_3$–$C_6$-cycloalkyl, phenyl, naphthalene, pyrrolidine, piperidine, morpholine, piperazine, pyridine, pyrimidine, triazine, pyrrole, thiophene, thiazole, imidazole, oxazole, isoxazole, pyrazole and thiadiazole, wherein each of the cyclic substituents is unsubstituted or substituted by $C_1$–$C_8$-alkyl, halogen, $OC_1$–$C_8$-alkyl, OH, $NO_2$ or $CF_3$.

8. The compound of formula I defined in claim 5 wherein
$R^1$ is H, $CO_2R^3$, $NR^3R^4$, $OR^4$ or $C_1$–$C_8$-alkyl which is unsubstituted or substituted by OH, $OC_1$–$C_8$-alkyl or halogen;
$R^3$ is H or $C_1$–$C_8$-alkyl which is unsubstituted or substituted by OH, $OC_1$–$C_8$-alkyl or halogen; and
wherein the optionally fused phenyl ring is unsubstituted or carries one or two substituents selected from the group consisting of: $OR^4$, $C_1$–$C_8$-alkyl, halogen, CN, $CO_2R^3$, $NO_2$, $SO_2R^3$, $SO_3R^3$, $NR^3R^4$, $SO_2NR^3R^4$, $SR^3$, $CF_3$, $CHF_2$, $C_3$–$C_6$-cycloalkyl, phenyl, naphthalene, pyrrolidine, piperidine, morpholine, piperazine, pyridine, pyrimidine, triazine, pyrrole, thiophene, thiazole, imidazole, oxazole, isoxazole, pyrazole and thiadiazole, wherein each of the cyclic substituents is unsubstituted or substituted by $C_1$–$C_8$-alkyl, halogen, $OC_1$–$C_8$-alkyl, OH, $NO_2$ or $CF_3$.

9. The compound of the formula I defined in claim 1 wherein A is $C_1$–$C_{10}$-alkylene or a group consisting of 1 to 10 methylene members and one or two radicals selected from the group consisting of O, S, $NR_3$, cyclohexylene, a double bond and a triple bond.

10. The compound of the formula I defined in claim 5 wherein A is $C_1$–$C_{10}$-alkylene or a group consisting of 1 to 10 methylene members and one or two radicals selected from the group consisting of O, S, $NR^3$, cyclohexylene, a double bond and a triple bond.

11. The compound of the formula I defined in claim 5 wherein
$R^1$ is H or $OR^4$, where $R^4$ is H, $C_3$–$C_6$-cycloalkyl or $C_1$–$C_8$-alkyl which is unsubstituted or substituted by OH, $OC_1$–$C_8$-alkyl or halogen;
$R^2$ is H, $C_1$–$C_8$-alkyl which is unsubstituted or substituted by OH, $OC_1$–$C_8$-alkyl or halogen, or $NR^3R^4$, where $R^3$ and $R^4$ are, independently of one another, H, phenyl-$C_1$–$C_8$-alkyl or $C_1$–$C_8$-alkyl, or $OR^4$ where $R^4$ is H or $C_1$–$C_8$-alkyl, or $CF_3$; and
Ar is phenyl which is unsubstituted or carries one, two, three or four substituents selected from the group consisting of $C_1$–$C_8$-alkyl which is unsubstituted or substituted by OH, $OC_1$–$C_8$-alkyl or halogen, or $OR^4$ where $R^4$ is H, $C_1$–$C_8$-alkyl which is unsubstituted or substituted by OH, $OC_1$–$C_8$-alkyl or halogen, or $CHF_2$, $CF_3$, CN, halogen, $C_2$–$C_6$-alkenyl, $C_2$–$C_6$-alkynyl, $C_3$–$C_6$-cycloalkyl, phenyl, naphthalene, pyrrolidine, piperidine, morpholine, piperazine, pyridine, pyrimidine, triazine, pyrrole, thiophene, thiazole, imidazole, oxazole, isoxazole, pyrazole and thiadiazole.

12. The compound of the formula I defined in claim 5 wherein
$R^1$ is H or $C_1$–$C_8$-alkyl which is unsubstituted or substituted by OH, $OC_1$–$C_8$-alkyl or halogen;
$R^2$ is H, $C_1$–$C_8$-alkyl which is unsubstituted or substituted by OH, $OC_1$–$C_8$-alkyl or halogen, or $NR^3R^4$ where $R^3$ and $R^4$ are, independently of one another, H or $C_1$–$C_8$-alkyl, or $OR^4$ where $R^4$ is H or $C_1$–$C_8$-alkyl, or $CF_3$;
A is $C_1$–$C_{10}$-alkylene or a group consisting of 1 to 10 methylene members and one member selected from the group consisting of oxygen, sulfur and $NR^3$;

Ar is phenyl which is unsubstituted or carries from one to four substituents selected from the group consisting of: CN, $SR^3$, halogen, $C_1$–$C_8$-alkyl which is unsubstituted or substituted by OH, $OC_1$–$C_8$-alkyl or halogen, or phenyl, naphthalene, $OR^4$, $NO_2$, $NR^3R^4$, $CHF_2$ and $CF_3$.

13. The compound of the formula I defined in claim 12 wherein

A is $SC_3$–$C_{10}$-alkylene, $OC_3$–$C_{10}$-alkylene or $NR^3$–$C_3$–$C_{10}$-alkylene, where $R^3$ is H or $C_1$–$C_8$-alkyl;

$R^1$ is H or $C_1$–$C_8$-alkyl;

Ar is phenyl which is unsubstituted or carries from one to four substituents selected from the group consisting of $C_1$–$C_8$-alkyl, $OC_1$–$C_8$-alkyl, $CHF_2$, $CF_3$ and CN.

14. The compound of the formula I defined in claim 13 wherein the phenyl ring Ar is substituted by one or two substituents which are located in position 3 and position 5, with one substituent being $CF_3$, $CHF_2$ or $C_1$–$C_8$-alkyl and the other substituent being H or $C_1$–$C_8$-alkyl.

15. The compound of the formula I defined in claim 1 wherein $R^1$ is H or $C_1$–$C_8$-alkyl which is unsubstituted or substituted by OH, $OC_1$–$C_8$-alkyl or halogen, $R^2$ is H, $NR^3R^4$ or $OR^4$ where $R^3$ and $R^4$ are, independently of one another, H, $C_1$–$C_8$-alkyl or phenyl-$C_1$–$C_8$-alkyl;

A is $C_1$–$C_{10}$-alkylene or is a group consisting of 1 to 10 methylene members and one or two members selected from the group consisting of O, S, $NR^3$ where $R^3$ is H or $C_1$–$C_8$-alkyl, a double bond and a triple bond.

16. The compound of the formula I defined in claim 5 wherein $R^1$ is H or $C_1$–$C_8$-alkyl which is unsubstituted or substituted by OH, $OC_1$–$C_8$-alkyl or halogen, $R^2$ is H, $NR^3R^4$ or $OR^4$ where $R^3$ and $R^4$ are, independently of one another, H, $C_1$–$C_8$-alkyl or phenyl-$C_1$–$C_8$-alkyl;

A is $C_1$–$C_{10}$-alkylene or is a group consisting of 1 to 10 methylene members and one or two members selected from the group consisting of O, S, $NR^3$ where $R^3$ is H or $C_1$–$C_8$-alkyl, a double bond and a triple bond.

17. A pharmaceutical composition containing the compound of formula I defined in claim 13 and a conventional pharmaceutical aid.

18. A method for treating a disorder which responds to dopamine $D_3$ receptor ligands, which comprises administering an effective amount of the compound of formula I defined in claim 1 to a person requiring such treatment.

19. The method of claim 18, wherein the disorder which responds to dopamine $D_3$ receptor ligands is schizophrenia, depression, a neurosis or a psychosis.

* * * * *